United States Patent

Borchert et al.

[11] Patent Number: 6,034,270
[45] Date of Patent: Mar. 7, 2000

[54] PROCESS FOR THE SELECTIVE PREPARATION OF ACETIC ACID USING A MOLYBDENUM, PALLADIUM, AND RHENIUM CATALYST

[75] Inventors: Holger Borchert, Bockenheim a.d. Weinstrasse; Uwe Dingerdissen, Seeheim-Jugenheim; Jens Weiguny, Freinsheim, all of Germany

[73] Assignee: Hoechst Research & Technology Deutschland GmbH & Co. KG, Frankfurt, Germany

[21] Appl. No.: 09/180,995

[22] PCT Filed: May 16, 1997

[86] PCT No.: PCT/EP97/02522

§ 371 Date: Nov. 19, 1998

§ 102(e) Date: Nov. 19, 1998

[87] PCT Pub. No.: WO97/44299

PCT Pub. Date: Nov. 27, 1997

[30] Foreign Application Priority Data

May 22, 1996 [DE] Germany .................. 196 20 542

[51] Int. Cl.⁷ ............... C07C 51/16; B01J 23/03
[52] U.S. Cl. ............ 562/548; 502/313; 502/321; 502/333; 562/549
[58] Field of Search ............. 562/548, 549; 502/313, 321, 333

[56] References Cited

FOREIGN PATENT DOCUMENTS 0 407 091 A1  1/1991  European Pat. Off. .
0 480 594 A2  4/1992  European Pat. Off. .

*Primary Examiner*—Gary Geist
*Assistant Examiner*—Robert W. Deemie
*Attorney, Agent, or Firm*—Frommer Lawrence & Haug LLP

[57] ABSTRACT

A process for the selective preparation of acetic acid from a gaseous feed comprising ethane, ethylene or mixtures thereof plus oxygen at elevated temperature, which comprises bringing the gaseous feed into contact with a catalyst comprising the elements Mo, Pd, Re, X and Y in gram atom ratios a:b:c:d:e in combination with oxygen $$Mo_a Pd_b Re_c X_d Y_e \quad (I)$$

where the symbols X, Y have the following meanings:

X=Cr, Mn, Nb, B, Ta, Ti, V and/or W
Y=Bi, Ce, Co, Cu, Te, Fe, Li, K, Na, Rb, Be, Mg, Ca, Sr, Ba, Ni, P, Pb, Sb, Si, Sn, Tl and/or U;
the indices a, b, c, d and e are the gram atom ratios of the corresponding elements, where
a=1, b>0, c>0, d=0.05–2, e=0–3.

9 Claims, No Drawings

PROCESS FOR THE SELECTIVE PREPARATION OF ACETIC ACID USING A MOLYBDENUM, PALLADIUM, AND RHENIUM CATALYST

The present invention relates to a process for the selective preparation of acetic acid by catalytic gas-phase oxidation of ethane and/or ethylene in the presence of a palladium-containing catalyst.

The oxidative dehydrogenation of ethane to ethylene in the gas phase at temperatures of >500° C. is known, for example from U.S. Pat. Nos. 4,250,346, 4,524,236 and 4,568,790.

Thus, U.S. Pat. No. 4,250,346 describes the use of a catalyst composition comprising the elements molybdenum, X and Y in the ratio a:b:c for converting ethane into ethylene, where X is Cr, Mn, Nb, Ta, Ti, V, and/or W and Y is Bi, Ce, Co, Cu, Fe, K, Mg, Ni, P, Pb, Sb, Si, Sn, Tl and/or U and a is 1, b is from 0.05 to 1 and c is from 0 to 2. The total value of c for Co, Ni and/or Fe must here by less than 0.5.

The reaction is preferably carried out in the presence of added water. The disclosed catalysts can likewise be used for the oxidation of ethane to give acetic acid, with the efficiency of the conversion to acetic acid being about 18%, at an ethane conversion of 7.5%.

The abovementioned documents are concerned mainly with the preparation of ethylene, less with the target preparation of acetic acid.

In contrast, EP-B-0 294 845 describes a process for the selective preparation of acetic acid from ethane, ethylene or mixtures thereof using oxygen in the presence of a catalyst mixture comprising at least A.) a calcined catalyst of the formula $Mo_xV_y$ or $Mo_xV_yZ_y$, where Z is one or more of the metals Li, Na, Be, Mg, Ca, Sr, Ba, Zn, Cd, Hg, Sc, Y, La, Ce, Al, Tl, Ti, Zr, Hf, Pb, Nb, Ta, As, Sb, Bi, Cr, W, U, Te, Fe, Co and Ni, and x is from 0.5 to 0.9, y is from 0.1 to 0.4 and z is from 0.001 to 1, and B.) an ethylene hydration catalyst and/or ethylene oxidation catalyst. The second catalyst component B is, in particular, a molecular sieve catalyst or a palladium-containing oxidation catalyst. When the catalyst mixture described is used and a gas mixture comprising ethane, oxygen, nitrogen and water vapor is passed through the catalyst-containing reactor, the maximum selectivity is 27% at an ethane conversion of 7%.

A further process for preparing a product comprising ethylene and/or acetic acid is described in EP-B-0 407 091. Here, ethane and/or ethylene and a gas comprising molecular oxygen is brought into contact at elevated temperature with a catalyst composition comprising the elements A, X and Y. A is here $Mo_dRe_eW_f$, X is Cr, Mn, Nb, Ta, Ti, V and/or W and Y is Bi, Ce, Co, Cu, Fe, K, Mg, Ni, P, Pb, Sb, Si, Sn, Tl and/or U. The maximum selectivities which were able to be achieved when using the catalyst described in the oxidation of ethane to acetic acid are 78%. Further by-products formed are carbon dioxide, carbon monoxide and ethylene.

However, none of the publications listed above describes the use of a catalyst comprising the elements rhenium, palladium and molybdenum for the selective oxidation of ethane and/or ethylene to give acetic acid. Furthermore, the selectivities achieved up to now in the prior art for the oxidation to acetic acid are still not satisfactory.

It is therefore an object of the invention to provide a process which allows ethane and/or ethylene to be oxidized in a simple and targeted manner and with high selectivity to give acetic acid.

It has now surprisingly been found that use of a catalyst comprising the elements molybdenum, rhenium and palladium and one or more elements selected from the group consisting of chromium, manganese, niobium, tantalum, titanium, vanadium and/or tungsten makes it possible to oxidize ethane and/or ethylene under relatively mild conditions, in a simple manner with high selectivity to give acetic acid.

The present invention accordingly provides a process for the selective preparation of acetic acid from a gaseous feed comprising ethane, ethylene or mixtures thereof plus oxygen at elevated temperature, which comprises bringing the gaseous feed into contact with a catalyst comprising the elements Mo, Pd, Re, X and Y in gram atom ratios a:b:c:d:e in combination with oxygen $$Mo_aPd_bRe_cX_dY_e \qquad (I)$$

where the symbols X, Y have the following meanings:

X=Cr, Mn, Nb, B, Ta, Ti, V and/or W, in particular Nb, V and W

Y=Bi, Ce, Co, Cu, Te, Fe, Li, K, Na, Rb, Be, Mg, Ca, Sr, Ba, Ni, P, Pb,

Sb, Si, Sn, Tl and/or U, in particular Ca, Sb, Te and Li.

The indices a, b, c, d and e are the gram atom ratios of the corresponding elements, where a=1, b>0, c>0, d=0.05–2 and e=0–3.

If X and Y are a plurality of different elements, the indices d and e can likewise assume a plurality of different values.

The present invention further provides a catalyst for the selective preparation of acetic acid comprising the elements Mo, Pd, Re, X and Y in the gram atom ratios a:b:c:d:e in combination with oxygen.

The gram atom ratios a:b:c:d:e are preferably within the following ranges:

a=1; b=0.0001–0.5; c=0.25–1.0; d=0.1–1.0; e=0–1.0.

Palladium contents in the catalyst which are above the upper limit specified promote the formation of carbon dioxide in the process of the invention. Furthermore, higher palladium contents are generally also avoided because they make the catalyst unnecessarily expensive. On the other hand, palladium contents below the limiting value specified favor ethylene formation.

Rhenium contents below the limiting value specified likewise lead to preferential formation of ethylene at the expense of the selectivity to acetic acid. On the other hand, rhenium contents which are higher than the limiting value specified give no further improvement in the catalytic properties and would therefore also just make the catalyst unnecessarily expensive.

The catalyst used according to the invention preferably comprises not only the elements molybdenum, palladium and rhenium but also vanadium, niobium, antimony and calcium in combination with oxygen. The gram atom ratios $a:b:c:d^1:d^2:e^1:e^2$ of the elements Mo:Pd:Re:V:Nb:Sb:Ca are preferably as follows:

a(Mo)=1; b(Pd)=0.0001–0.5, in particular 0.001–0.05;

c(Re)=0.25–1.0; $d^1$(V)=0.2–1.0; $d^2$(Nb)=0.1–0.5;

$e^1$(Sb)=0–0.5; $e^2$(Ca)=0–0.2;

Examples of such catalyst compositions which are preferably used in the process of the invention are:

$Mo_{1.0}Pd_{0.01}Re_{0.7}V_{0.7}Nb_{0.2}Sb_{0.1}Ca_{0.05}$ $Mo_{1.0}Pd_{0.02}Re_{0.7}V_{0.7}Nb_{0.2}Sb_{0.1}Ca_{0.05}$ $Mo_{1.0}Pd_{0.02}Re_{0.5}V_{0.5}Nb_{0.5}Sb_{0.1}$ $Mo_{1.0}Pd_{0.02}Re_{0.7}V_{0.5}Te_{0.5}$ $Mo_{1.0}Pd_{0.02}Re_{0.7}V_{0.7}Nb_{0.2}Sb_{0.1}Ca_{0.05}$ $Mo_{1.0}Pd_{0.02}Re_{0.7}W_{0.2}V_{0.7}Nb_{0.2}Sb_{0.1}$

The catalysts used according to the invention can be prepared by conventional methods. These start out from a slurry, in particular an aqueous solution, comprising the individual starting components of the elements in accordance with their proportions.

The starting materials for the individual components in the preparation of the catalyst of the invention are, apart from the oxides, preferably water-soluble substances such as ammonium salts, nitrates, sulfates, halides, hydroxides and salts of organic acids which can be converted into the corresponding oxides by heating. To mix the components, aqueous solutions or suspensions of the metal salts are prepared and mixed.

In the case of molybdenum, it is advisable to use the corresponding molybdates e.g. ammonium molybdate, as starting compounds because of their commercial availability.

Suitable palladium compounds are, for example, palladium(II) chloride, palladium(II) sulfate, tetramminepalladium(II) nitrate, palladium(II) nitrate and also palladium(II) acetylacetonate.

In the case of rhenium, it is possible to use, for example, perrhenic acid, ammonium perrhenate and also rhenium(III) and rhenium(V) chlorides, to name only a few, as starting compound.

The reaction mixture obtained is then stirred at from 50 to 100° C. for from 5 minutes to 5 hours. The water is subsequently removed and the remaining catalyst is dried at a temperature of from 50 to 150° C., in particular from 80 to 120° C.

If the catalyst obtained is subsequently subjected to a calcination process, it is advisable to calcine the dried and pulverized catalyst at a temperature in the range from 100° C. to 800° C., in particular from 200 to 500° C., in the presence of nitrogen, oxygen or an oxygen-containing gas. The duration is from 2 to 24 hours.

The catalyst can be used without a support material or be mixed with an appropriate support material or applied thereto. Suitable support materials are the customary materials such as porous silicon dioxide, ignited silicon dioxide, kieselguhr, silica gel, porous or nonporous aluminum oxide, titanium dioxide, zirconium dioxide, thorium dioxide, lanthanum oxide, magnesium oxide, calcium oxide, barium oxide, tin oxide, cerium dioxide, zinc oxide, boron oxide, boron nitride, boron carbide, boron phosphate, zirconium phosphate, aluminum silicate, silicon nitride or silicon carbide, but also meshes made of glass or metals.

Preferred support materials have a surface area of less than 100 m$^2$/g. Preferred support materials are silicon dioxide and aluminum oxide having a low specific surface area. The catalyst can, after shaping, be used as a regularly or irregularly shaped support body or else in powder form as a heterogeneous oxidation catalyst.

The reaction can be carried out in a fluidized bed or in a fixed-bed reactor. For use in a fluidized bed, the catalyst is milled to a particle size in the range from 10 to 200 μm.

The gaseous feed comprises ethane and/or ethylene which are fed to the reactor as pure gases or in admixture with one or more other gases. Suitable additional or carrier gases of this type are, for example, nitrogen, methane, carbon monoxide, carbon dioxide, air and/or water vapor. The gas containing molecular oxygen can be air or a gas containing more or less molecular oxygen than air, e.g. oxygen. Preference is given to adding water vapor to the gas comprising ethane and molecular oxygen since this promotes the selectivity to acetic acid. The proportion of water vapor is in the range from 5 to 30% by volume, preferably from 0 to 20% by volume. Lower water vapor contents lead to a loss of selectivity in respect of acetic acid formation, while higher water vapor concentrations would make the work-up of the resulting aqueous acetic acid unnecessarily more expensive for technical process reasons. The addition of oxygen or the gas comprising molecular oxygen depends on the explosive limits under the reaction conditions. Relatively high oxygen contents are preferred, since the achievable ethane conversion and thus the yield of acetic acid is higher. The maximum oxygen concentration is, however, limited by the explosive limits. The ratio of ethane to oxygen is advantageously in the range between 1:1 and 10:1, preferably 2:1 and 8:1.

The reaction is carried out at temperatures between 200 and 500° C., preferably from 200 to 400° C. The pressure can be atmospheric or superatmospheric, e.g. in the range between 1 and 50 bar, preferably from 1 to 30 bar.

The reaction can be carried out in a fixed-bed or fluidized-bed reactor. Advantageously, ethane is first mixed with the inert gases such as nitrogen or water vapor before oxygen or the gas containing molecular oxygen is fed in. The mixed gases are preferably preheated to the reaction temperature in a preheating zone before the gas mixture is brought into contact with the catalyst. Acetic acid is separated from the gas leaving the reactor by condensation. The remaining gases are recirculated to the reactor inlet where oxygen or the gas containing molecular oxygen plus ethane and/or ethylene are metered in.

When using the catalyst of the invention, the selectivity in the oxidation of ethane and/or ethylene to acetic acid is >75 mol %, preferably >80 mol %, in particular >85 mol %, at an ethane conversion of >3%, preferably >4%, in particular >5%, so that, in comparison with the prior art, the process of the invention enables an increase in the acetic acid yields to be achieved in a simple manner while simultaneously reducing the formation of undesired by-products.

EXAMPLES

The catalyst compositions specified in the examples are given in relative atom ratios.

Catalyst Preparation

Catalyst (I)

A catalyst comprising the elements in the following composition (in combination with oxygen) was prepared:

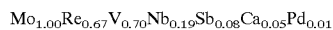

$Mo_{1.00}Re_{0.67}V_{0.70}Nb_{0.19}Sb_{0.08}Ca_{0.05}Pd_{0.01}$

Solution 1
  10.0 g of ammonium perrhenate, 0.12 g of palladium acetate and 9.7 g of ammonium molybdate in 50 ml of water.
Solution 2
  4.5 g of ammonium metavanadate in 50 ml of water.
Solution 3
  6.5 g of niobium oxalate, 1.34 g of antimony oxalate, 0.58 g of calcium nitrate in 180 ml of water.

The solutions are stirred separately at 70° C. for 15 minutes. The third solution is then added to the second. The combined mixtures are stirred at 70° C. for 15 minutes before they are added to the first. The resulting mixture is stirred at 70° C. for 15 minutes. The water is subsequently removed on a hot plate until a thick paste is formed. This is dried at 120° C. overnight. The solid is crushed (sieve fraction: 0.35–2 mm) and subsequently calcined in static air at 300° C. for 5 hours. The catalyst is then sieved in order to obtain a sieve fraction between 0.35 and 1 mm.

Catalyst (II)

A catalyst comprising the elements in the following composition (in combination with oxygen) was prepared:

$$Mo_{1.00}Re_{0.67}V_{0.70}Nb_{0.19}Sb_{0.08}Ca_{0.05}Pd_{0.02}$$

The preparation was carried out as described in Catalyst Example (I) except that 0.24 g instead of 0.12 g of palladium acetate was used.

Comparative Example

Catalyst (III)

For comparison, a catalyst corresponding to EP 0 407 091 and having the following composition was prepared:

$$Mo_{1.00}Re_{0.67}V_{0.70}Nb_{0.19}Sb_{0.08}Ca_{0.05}$$

The preparation was carried out as described in Catalyst Example (I) except that no palladium acetate was used.

The conversion of 14.3% reported in EP-B-0 407 091, Table 2, cannot be achieved for stoichiometric reasons even with complete conversion of the oxygen. At the selectivities indicated and the composition of the feed gas, the conversion can be at most 5.9%. In this calculation, it was assumed that only carbon monoxide is formed in addition to acetic acid and ethylene. If carbon dioxide is formed instead of carbon monoxide, the maximum achievable ethane conversion is only 5.5%. It may be assumed that, owing to the experimental procedure, ethane was condensed in the cold trap located downstream of the reactor, which led to the incorrect calculation of an excessively high conversion. To compare the catalytic properties of this catalyst with the catalyst of the invention, both catalysts were tested under identical reaction conditions (see comparative example).

Method of Catalyst Testing

A steel reactor having an internal diameter of 10 mm was charged with 10 ml of the catalyst. The catalyst was heated to 250° C. under a stream of air. The pressure was subsequently set by means of an admission pressure regulator. The desired ethane: oxygen: nitrogen mixture was metered together with water into a vaporizer zone where water was vaporized and mixed with the gases. The reaction temperature was measured using a thermocouple in the catalyst bed. The reaction gas was analyzed on-line by gas chromatography.

In the examples, the following terms are defined as:

ethane conversion (%)=100×([CO]/2+[CO$_2$]/2+[C$_2$H$_4$]+ [CH$_3$COOH])/([CO]/2+[CO$_2$]/2+[C$_2$H$_4$]+[C$_2$H$_6$]+ [CH$_3$COOH])

Ethylene selectivity (%)=100×([C$_2$H$_4$])/([CO]/2+[CO$_2$]/ 2+[C$_2$H$_4$]+[CH$_3$COOH])

Acetic acid selectivity (%)=100×([CH$_3$COOH])/([CO]/2+ [CO$_2$]/2+[C$_2$H$_4$]+[CH$_3$COOH])

where

[ ]=concentrations in mol % and

[C$_2$H$_6$]=concentration of the unreacted ethane.

The residence time is defined as:

t(s)=bed volume of the catalyst (ml)/volume flow of the gas through the reactor based on the reaction conditions (ml/s).

Reaction Procedure

The reaction was carried out at 280° C. and 15 bar. The feed gas to the reactor consisted of 40% by volume of ethane, 8% by volume of oxygen, 32% by volume of nitrogen and 20% by volume of water vapor. The results are summarized in the following table.

| Catalyst | Residence time (s) | Ethane conversion (%) | Acetic acid selectivity (%) | Ethylene selectivity (%) | CO + CO$_2$ selectivity (%) |
|---|---|---|---|---|---|
| (I) | 30 | 3 | 91 | 0 | 9 |
| (II) | 30 | 4 | 91 | 0 | 9 |
| (II) | 60 | 8 | 90 | 2 | 8 |
| (III) | 30 | 5 | 61 | 29 | 10 |

Compared to Catalyst (III), Catalysts (I) and (II) give higher selectivities to acetic acid without the CO+CO$_2$ selectivities being increased. This leads to an improved acetic acid yield based on the amount of catalyst used and the ethane feed stream.

We claim:

1. A process for the selective preparation of acetic acid from a gaseous feed comprising ethane, ethylene or mixtures thereof plus oxygen at elevated temperature, which comprises bringing the gaseous feed into contact with a catalyst comprising the elements Mo, Pd, Re, X and Y in gram atom ratios a:b:c:d:e in combination with oxygen $$Mo_aPd_bRe_cX_dY_e \qquad (I)$$

where the symbols X, Y have the following meanings:

X=Cr, Mn, Nb, B, Ta, Ti, V and/or W;

Y=Bi, Ce, Co, Cu, Te, Fe, Li, K, Na, Rb, Be, Mg, Ca, Sr, Ba, Ni, P, Pb, Sb, Si, Sn, Tl and/or U;

the indices a, b, c, d and e are the gram atom ratios of the corresponding elements, where a=1, b>0, c>0, d=0.05–2, e=0–3.

2. The process as claimed in claim 1, wherein the reaction temperature is in the range from 200 to 500° C.

3. The process as claimed in claim 1, wherein the pressure in the reactor is in the range from 1 to 50 bar.

4. The process as claimed in claim 1, wherein b=0.0001–0.5.

5. The process as claimed in claim 1, wherein ethane mixed with at least one further gas, in particular nitrogen, methane, carbon dioxide, carbon monoxide, ethylene and/or water vapor, is fed to the reactor.

6. The process as claimed in claim 1, wherein the catalyst comprises at least one of the following compositions in combination with oxygen:

$Mo_{1.0}Pd_{0.01}Re_{0.7}V_{0.7}Nb_{0.2}Sb_{0.1}Ca_{0.05}$ $Mo_{1.0}Pd_{0.02}Re_{0.7}V_{0.7}Nb_{0.2}Sb_{0.1}Ca_{0.05}$ $Mo_{1.0}Pd_{0.02}Re_{0.5}V_{0.5}Nb_{0.5}Sb_{0.1}$ $Mo_{1.0}Pd_{0.02}Re_{0.7}V_{0.5}Te_{0.5}$ $Mo_{1.0}Pd_{0.02}Re_{0.7}V_{0.7}Nb_{0.2}Sb_{0.1}Ca_{0.05}$ $Mo_{1.0}Pd_{0.02}Re_{0.7}W_{0.2}V_{0.7}Nb_{0.2}Sb_{0.1}$

7. The process as claimed in claim 1, wherein the selectivity of the oxidation reaction of ethane and/or ethylene to form acetic acid is >75 mol %, at an ethane conversion of >3%.

8. The process as claimed in claim 1, wherein the catalyst is mixed with a support material or is fixed on a support material.

9. A catalyst for the selective oxidation of ethane and/or ethylene to form acetic acid, comprising the elements Mo, Pd, Re, X and Y in the gram atom ratios a:b:c:d:e in combination with oxygen $$Mo_aPd_bRe_cX_dY_e \qquad (I)$$

where the symbols X, Y have the following meanings:
   X=Cr, Mn, Nb, B, Ta, Ti, V and/or W;
   Y=Bi, Ce, Co, Cu, Te, Fe, Li, K, Na, Rb, Be, Mg, Ca, Sr, Ba, Ni, P, Pb, Sb, Si, Sn, Tl and/or U;
   the indices a, b, c, d and e are the gram atom ratios of the corresponding elements, where
   a=1, b>0, c>0, d=0.05–2, e=0–3.

* * * * *